United States Patent [19]

Reich et al.

[11] Patent Number: 4,992,604

[45] Date of Patent: Feb. 12, 1991

[54] STABILIZED 1,1,1-TRICHLOROETHANE COMPOSITIONS

[75] Inventors: Donald A. Reich; Catherine C. Doyen, both of Lake Charles, La.; Stephanie J. Oates, Wadsworth, Ohio

[73] Assignee: PPG Industries, Inc., Pittsburgh, Pa.

[21] Appl. No.: 383,488

[22] Filed: Jul. 24, 1989

[51] Int. Cl.$^5$ ...................... C07C 17/42; C07C 19/05
[52] U.S. Cl. .................................................... 570/110
[58] Field of Search ......................................... 570/110

[56] References Cited

U.S. PATENT DOCUMENTS

| | | | |
|---|---|---|---|
| 3,238,137 | 3/1966 | Grammer et al. | 252/171 |
| 3,251,891 | 5/1966 | Cormany et al. | 260/652.5 |
| 3,265,747 | 8/1966 | Cormany et al. | 260/652.5 |
| 3,281,480 | 10/1966 | Hardies | 260/652.5 |
| 3,285,857 | 11/1966 | Rathbone et al. | 252/171 |
| 3,505,415 | 4/1970 | Richtzenhain et al. | 570/110 |
| 3,532,761 | 10/1970 | Manner | 260/652.5 |
| 3,549,715 | 12/1970 | Cormany et al. | 260/652.5 |
| 3,564,061 | 2/1971 | Correia et al. | 260/652.5 |
| 3,848,004 | 11/1974 | Katsuragaw et al. | 260/652.5 R |
| 3,878,256 | 4/1975 | Richtzenhain et al. | 260/652.5 R |
| 4,016,215 | 4/1977 | Otsuki et al. | 570/110 |
| 4,018,837 | 4/1977 | Archer et al. | 260/652.5 R |
| 4,026,956 | 5/1977 | Manner | 260/652.5 |
| 4,069,265 | 1/1978 | Richtzenhain et al. | 260/652.5 R |
| 4,115,461 | 9/1978 | Spencer et al. | 260/652.5 R |
| 4,356,038 | 10/1982 | Bain et al. | 134/2 |
| 4,418,231 | 11/1983 | Pamer | 570/115 |
| 4,466,903 | 8/1984 | Pamer | 252/392 |
| 4,783,560 | 11/1988 | Servais et al. | 570/110 |
| 4,795,837 | 1/1989 | Servais | 570/110 |
| 4,804,493 | 2/1989 | Gorski | 252/172 |

FOREIGN PATENT DOCUMENTS

| | | |
|---|---|---|
| 0024113 | 11/1983 | European Pat. Off. |
| 127404 | 11/1978 | Japan ................................. 570/110 |
| 1045068 | 10/1966 | United Kingdom . |
| 1435548 | 5/1976 | United Kingdom . |
| 1439970 | 6/1976 | United Kingdom . |
| 2024242 | 1/1980 | United Kingdom . |
| 2024243 | 1/1980 | United Kingdom . |

*Primary Examiner*—J. E. Evans
*Attorney, Agent, or Firm*—George D. Morris

[57] ABSTRACT

1,1,1-Trichloroethane (viz., methylchloroform) is stabilized with from about 2 to about 4 percent by weight 1,3-dioxolane, from about 0.25 to about 0.5 percent by weight butylene oxide, from about 0.25 to about 2 percent by weight nitromethane, from about 0.2 to about 0.75 percent by weight 1-nitropropane, from about 0.75 to about 2 percent by weight secondary butanol, and from 0 to about 100 parts per million by weight acetaldehyde dimethylhydrazone.

6 Claims, No Drawings

STABILIZED 1,1,1-TRICHLOROETHANE COMPOSITIONS 1,1,1-Trichloroethane (viz., methylchloroform) has highly advantageous properties as a solvent, but because it is reactive with metals such as aluminum, magnesium, zinc, and their alloys, and with water and various metal halides (particularly the Friedel-Crafts metal halides as for example, aluminum chloride), the pure material is only rarely used for these purposes. It has therefore been customary for many years to add small amounts of one or more compounds which reduce the tendency of 1,1,1-trichloroethane to decompose and/or perform one or more other functions such as removal of acid species. These compounds are commonly referred to individually as "stabilizers" and mixtures of these compounds are commonly referred to as "stabilizer systems."

1,1,1-Trichloroethane presents its own unique difficulties regarding stabilization, and experiences in the stabilization of other halogenated hydrocarbons are not applicable. Nevertheless many stabilizers and stabilizer systems for 1,1,1-trichloroethane are known. It has been found, however, that modifying known stabilizer systems even by the deletion, substitution, or addition of known stabilizers often causes differences in overall performance. Gross differences in performance resulting from gross modifications in composition are generally fairly predictable, but subtle differences resulting from subtle modifications are generally not. For example, if acid acceptor is totally eliminated from a stabilizer system, one could reasonably predict that aqueous extracts of the stabilized 1,1,1-trichloroethane would probably show the rather rapid accumulation of acid species in the stabilized 1,1,1-trichloroethane as it is used as an industrial solvent. However, the substitution of one acid acceptor for another often gives rise to unpredictable subtle results, since the new acid acceptor may not only result in unexpected differences in acid accepting performance, but it may also affect the performance of other stabilizers present for other purposes. Yet other considerations affect the selection of stabilizers. In the better stabilizer systems, the stabilizers are such that when the stabilized 1,1,1-trichloroethane composition is used for vapor degreasing, there is an adequate distribution of the stabilizers in both the liquid and vapor phases so that the 1,1,1-trichloroethane is stabilized in both phases. This places severe constraints on the selection of stabilizers. Still other considerations include the effectiveness of a stabilizer in performing its function, its reactivity, and its lifetime as an effective stabilizer. The foregoing are illustrative of the multiplicity of the factors to be considered, but they are by no means exhaustive. In summary, the search for new stabilizer systems goes on, often using only known stabilizers, in order to produce slight but beneficial differences in overall performance. Such fine tuning is ultimately guided by the results of empirical experimentation rather than theoretical extrapolation.

One of the more effective stabilizers for stabilization of 1,1,1-trichloroethane against metal/metal halide induced decomposition is 1,4-dioxane. This compound not only has the foregoing property, but it also serves to promote film-wise evaporation of solvent from a workpiece. With the continued accumulation of evidence of the adverse toxicological properties of 1,4-dioxane, omission of this substance from stabilized 1,1,1-trichloroethane formulations has become desirable.

A stabilizer that is effective in stabilizing 1,1,1-trichloroethane against metal/metal halide induced decomposition is 1,3-dioxolane, but this compound does not effectively promote film-wise evaporation. As stabilized 1,1,1-trichloroethane in which 1,4-dioxane has been replaced by 1,3-dioxolane evaporates, the liquid on the workpiece eventually breaks up into droplets. With continued evaporation from the droplets, dissolved grease and entrained dirt are concentrated as the sizes of the droplets decrease. The final result is a workpiece having localized spots of grease and/or dirt distributed over its surface.

Stabilized 1,1,1-trichloroethane compositions have now been discovered which exhibit balanced properties of stabilization against metal/metal halide induced decomposition, of film-wise evaporation, of low accumulation of acid species, and of adequate distribution of the stabilizers in both liquid and vapor phases. Accordingly, the present invention is stabilized 1,1,1-trichloroethane composition which is substantially free of 1,4-dioxane and which consists essentially of (a) 1,1,1-trichloroethane, (b) from about 2 to about 4 percent by weight 1,3-dioxolane, (c) from about 0.25 to about 0.5 percent by weight butylene oxide, (d) from about 0.25 to about 2 percent by weight nitromethane, (e) from about 0.2 to about 0.75 percent by weight 1-nitropropane, (f) from about 0.75 to about 2 percent by weight secondary butanol, and (g) from 0 to about 100 parts per million by weight acetaldehyde dimethylhydrazone.

Preferably, but not necessarily, the concentration of all stabilizers in the stabilized 1,1,1-trichloroethane composition is not in excess of about 7 percent by weight, as this ensures that the composition will not be in the flammability range.

The 1,3-dioxolane, nitromethane, and secondary butanol retard or prevent metal induced and metal halide induced decomposition of 1,1,1-trichloroethane. Although 1-nitropropane is itself not very effective in reducing metal induced decomposition of 1,1,1-trichloroethane, it is effective in promoting film-wise evaporation and is included for this purpose. The butylene oxide (which may be 1,2-butylene oxide, 2,3-butylene oxide, or a mixture of both such isomers) reacts with HCl that may form. The acetaldehyde dimethylhydrazone eliminates or retards peroxide formation characteristic of some stabilizers; its use is optional.

In many cases the 1,3-dioxolane is present in the stabilized 1,1,1-trichloroethane composition in an amount in the range of from about 2.3 to about 3 percent by weight. From about 2.5 to about 2.7 percent by weight is preferred.

The butylene oxide is frequently present in the stabilized 1,1,1-trichloroethane composition in an amount in the range of from about 0.27 to about 0.48 percent by weight. From about 0.3 to about 0.45 percent by weight is preferred.

Often the nitromethane is present in the stabilized 1,1,1-trichloroethane composition in an amount in the range of from about 0.3 to about 1 percent by weight. From about 0.5 to about 0.7 is preferred.

The 1-nitropropane is in many cases present in the stabilized 1,1,1-trichloroethane composition in an amount in the range of from about 0.25 to about 0.65 percent by weight. From about 0.35 to about 0.55 percent by weight is preferred.

The secondary butanol is often present in the stabilized 1,1,1-trichloroethane composition in an amount in the range of from about 0.8 to about 1.5 percent by weight. From about 1 to about 1.2 percent by weight is preferred.

When used, the acetaldehyde dimethylhydrazone is frequently present in the stabilized 1,1,1-trichloroethane composition in an amount in the range of from about 5 to about 100 parts per million by weight. Often it is present in an amount in the range of from about 5 to about 15 parts per million by weight. About 10 parts per million by weight is preferred.

The chief component of the stabilized composition is 1,1,1-trichloroethane. Minor amounts of other chlorinated hydrocarbon solvents (as for example, trichloroethylene, perchloroethylene, methylene chloride, and the like) may be added, but preferably the chlorinated hydrocarbon solvent present is substantially all 1,1,1-trichloroethane. It should be understood, however, that the normal impurities ordinarily present in industrial grade 1,1,1-trichloroethane are usually present in their usual amounts. In most cases 1,1,1-trichloroethane constitutes at least about 80 percent by weight of the stabilized composition. Often the 1,1,1-trichloroethane constitutes at least about 90 percent by weight of the stabilized composition. Frequently the 1,1,1-trichloroethane constitutes at least about 93 percent by weight of the stabilized composition.

The stabilized composition may be prepared by admixing the components in any order. For example, a stabilizer system may be first prepared by admixing some or all of the stabilizers together in the desired proportions and then the stabilized composition may be formed by admixing the stabilizer system and the 1,1,1-trichloroethane in the desired proportions. Usually, however, the stabilizers are admixed sequentially with the 1,1,1-trichloroethane-rich composition.

The stabilized 1,1,1-trichloroethane compositions of the invention find considerable uses, especially as a solvent, and particularly for industrial purposes. Examples of uses for these stabilized 1,1,1-trichloroethane compositions include the degreasing of metals, the defluxing of soldered circuit boards, the drycleaning of textiles, and in aerosols. Vapor phase degreasing, liquid phase degreasing, vapor phase defluxing, and liquid phase defluxing are all illustrative operations in which the stabilized 1,1,1-trichloroethane compositions of the present invention may be used.

As the stabilized composition is used for its intended purpose, it is expected that it will accumulate materials normally associated with used stabilized 1,1,1-trichloroethane compositions, such as dissolved grease, dirt, solder flux, and the like, as well as acid precursors, acid species, metal salts, water, and stabilizer reaction products. As used herein and in the claims, the recited proportions are in respect of the stabilized composition normalized to exclude for calculational purposes the accumulated materials.

The invention is further described in conjunction with the following examples which are to be considered illustrative rather than limiting, and in which all parts by weight and all percentages are percentages by weight unless otherwise specified.

The pH/titer tests are conducted as follows. A dilute sodium chloride solution is prepared by dissolving 1 gram sodium chloride in 1 gallon neutral distilled water. A 25 milliliter sample of the solvent composition to be tested is placed in a 250 milliliter beaker containing 75 milliliters of the dilute sodium chloride solution. The charged materials are mechanically stirred while the pH is determined using a pH meter employing a glass electrode and a calomel electrode. Depending on the pH observed, the sample is titrated with 0.01 N sodium hydroxide or 0.01 N hydrochloric acid until a neutral value of pH 7 is obtained. The material is considered to be neutral when it retains a pH in the range of from 7.0 to 7.3 for at least 30 seconds. The titer is reported as the milliliters of 0.01 N sodium hydroxide or 0.01 N hydrochloric acid used to obtain neutrality.

The acid acceptance test is conducted as follows. Hydrochlorinating reagent is prepared by adding 4.4 milliliters of concentrated hydrochloric acid (CP, 37%) to 200 milliliters of isopropanol (CP) and diluting to 500 milliliters with isopropanol. The resulting reagent is about 0.1 N HCl. Sodium hydroxide reagent is prepared by dissolving 50 grams of sodium hydroxide (CP) in 50 milliliters of distilled water in a 250 milliliter Pyrex ® beaker. The resulting solution is cooled and transferred to a 250 milliliter Pyrex flask. The flask is stoppered and the solution is allowed to stand quiescently for several days. (To save time, the solution may alternatively be filtered through a glass-fritted crucible, but carbon dioxide must be excluded during filtration.) Six and one-half milliliters of the clear solution is pipetted into a 1000 milliliter volumetric flask and diluted to the mark with recently boiled and cooled distilled water. The resulting sodium hydroxide reagent is about 0.1 N NaOH. The sodium hydroxide reagent is standardized by titrating one gram of Bureau of Standards acid potassium phthalate #84 dissolved in 50 milliliters of cool (25°–27.8° C.) water free of carbon dioxide and 3 drops of 0.2% phenolphthalein solution with the sodium hydroxide reagent. Bromophenol blue indicator is prepared by dissolving one gram of bromophenol blue in 800 milliliters of distilled water and 200 milliliters of denatured ethanol (U.S. Treasury Grade 4B). Exactly 25 milliliters of hydrochlorinating reagent and 25 milliliters of isopropanol is added to exactly 10 milliliters of the solvent composition in a 250 milliliter glass-stoppered Erlenmeyer flask. The flask is stoppered and the liquid is agitated well and then allowed to stand for 10 minutes at room temperature. Three drops of bromophenol blue indicator is added and the liquid titrated to the blue-green end point with the sodium hydroxide reagent. A blank titer is run by titrating exactly 25 milliliters of hydrochlorinating reagent and 3 drops of bromophenol blue indicator to the blue-green end point with sodium hydroxide reagent. The percent acid acceptance is calculated as:

$$\text{Acid Acceptance, percent} = \frac{(a - b) \times N \times 4.0}{v \times d}$$

where a = the milliliters of sodium hydroxide reagent required to titrate the blank, b = the milliliters of sodium hydroxide reagent required to titrate the sample, N = the normality of the sodium hydroxide reagent, v = the volume of sample expressed in milliliters, and d = the density of the sample expressed in grams per milliliter.

The blade aluminum scratch test is conducted as follows. A scribe is made from a 127 to 177.8 millimeter diameter stainless steel rod. One end is ground to a knife edge so that the edge is at a 45 degree angle to the axis of the rod. The other end is inserted into a rubber stopper or a wooden file handle. A 59.15 milliliter widemouthed bottle is clamped to a table. A 2024 alloy aluminum test strip measuring 12.7 millimeters by 41.275 millimeters by 1.5875 millimeters is placed in the bottle. Sufficient solvent composition is added to cover the entire strip. Three scratches are slowly made the length of the strip with the scribe blade while maximum pressure is exerted on the scribe by the operator. The sample is then allowed to stand undisturbed for 24 hours with the bottle cap lying (not tightened) on the top of the bottle. A numerical value is assigned for the appearance of the solvent, precipitate and strip after 24 hours and an average figure is reported. The rating system is shown in Table I. In the case of complete solvent decomposition, the formulation is given a rating of 10. The scribe is resharpened with a file after each test.

TABLE 1

| Blade-Aluminum Scratch Test Rating System | | | | | |
|---|---|---|---|---|---|
| Solvent | | Precipitate or Haze | | Strip | |
| Color | Rating | Condition | Rating | Condition | Rating |
| Colorless | 1 | None | 1 | No scar or solid on strip | 1 |
| Slight color | 2 | Slight haze | 2 | Very sl. white solid in scratch | 2 |
| Yellow or med. amber | 3 | Haze and/or sl. ppt. | 3 | Sl. scar or solid in scratch | 3 |
| Dark amber | 4 | Precipitate | 4 | Scar | 4 |
| Black | 5 | Heavy precipitate | 5 | Enlarged scar | 5 |

The aluminum turnings-cutting oil reflux test is conducted as follows. A 500 milliliter Erlenmeyer flask having a ground glass outer joint is tarred and charged with 20 grams Houghton 3105 cutting oil, 300 milliliters of the solvent to be tested, 45 milliliters Penreco Dakeol 35 mineral oil USP, 7.5 milliliters Mobilmet Omega cutting oil, 8 grams 2024 alloy aluminum chips, 8 grams 7075 alloy aluminum chips, several silica boiling chips and three 12.7 millimeter by 31.75 millimeter by 1.5875 millimeter mild steel strips which have been etched with concentrated hydrochloric acid, rinsed with water, dried, buffed with a wire wheel, rinsed with acetone, and dried. A copper wire is run through a water-cooled condenser and bent over the top rim. A 2.38125 millimeter hole is drilled in a buffed 2024 alloy aluminum strip measuring 12.7 millimeters by 76.2 millimeters. The aluminum strip is rinsed with acetone, dried, and hooked to the copper wire so that condensate will run down the suspended strip. The contents of the flask are thoroughly mixed and a 50 milliliter portion of the solvent and oil mixture is removed to a tarred graduate. The weight of the mixture is recorded and the density is calculated. The flask joint is connected to the condenser using a polytetrafluoroethylene sleeve. A hot plate is placed under the flask and the time at which refluxing begins is noted. Using a hypodermic syringe and needle, 50 milliliter samples of liquid are withdrawn through the condenser after refluxing 24 hours and 48 hours, respectively. After refluxing a total of 168 hours, heating is terminated and a sample of the liquid is taken. The samples are tested for pH/titer and acid acceptance. Appearances are noted after refluxing 168 hours.

The galvanized steel reflux test is conducted as follows: A 12.7 millimeter by 101..6 milliliter by 1.5875 millimeter galvanized steel strip which has been immersed in 2.5 percent chromic acid at 48° C. to 60° C. for 5 minutes, washed thoroughly for at least 5 minutes with distilled water, rinsed with acetone, and dried, is placed in a 500 milliliter Erlenmeyer flask having a ground glass joint. When the test is to be conducted under hydrous conditions, 2 milliliters of water is added; otherwise, the test is considered as being conducted under anhydrous conditions. Next, 250 milliliters of the solvent to be tested is added to the flask, resulting in immersion of about one-half of the steel strip. The flask is fitted with a water-cooled reflux condenser, placed on a hot plate and refluxed for 24 hours. The color of the liquid and appearance of the strip are ascertained. A sample of the liquid is tested according to the pH/titer tests described above, and the water soluble chlorides are determined.

The aluminum and aluminum chloride stability test is conducted as follows. One-half gram of anhydrous aluminum chloride is added to 50 milliliters of solvent composition in a 125 milliliter Erlenmeyer flask. One gram each of Alloy 2025 and Alloy 7075 aluminum chips is added. A water-cooled total reflux condenser is attached and the liquid is heated to boiling and refluxed for 24 hours on a hot plate. Appearance and odor are observed after the 24 hour reflux.

EXAMPLE I

The following materials were admixed with industrial grade 1,1,1-trichloroethane to form a stabilized 1,1,1-trichloroethane composition. The concentrations are percentages by weight and are in respect of the final stabilized composition:

| Component | Concentration, percent by weight |
|---|---|
| Nitromethane | 0.50 |
| 1,3-dioxolane | 2.0 |
| Secondary Butanol | 1.0 |
| Butylene Oxide (mixed isomers) | 0.30 |
| 1-Nitropropane | 0.50 |
| Acetaldehyde Dimethylhydrazone | 0.001 |

The distillation range of the stabilized 1,1,1-trichloroethane composition was found to be 73.2° C. to 83.3° C. The specific gravity, 25° C./25° C., was 1.314. Initial pH/titer was 6.4/0.40. Acid acceptance was 0.163 percent.

pH/titer of the base solvent, i.e., the 1,1,1-trichloroethane without added stabilizers) was 6.1/0.60.

A sample of the stabilized composition was evaporated from an inclined plane. No beading, uneven evaporation, and some streaking were observed.

The stabilized 1,1,1-trichloroethane composition was tested according to the blade aluminum scratch test. The results of three replicates were 1.3, 1.3, 2.

The stabilized 1,1,1-trichloroethane composition was tested according to the aluminum turnings cutting oil reflux test. The results are shown in Tables 1 and 2.

TABLE 1

| Results of Aluminum Turnings Cutting Oil Reflux Test | | |
|---|---|---|
| Reflux Time, hours | pH/Titer | Acid Acceptance, percent |
| 0 | 4.1/1.2 | 0.132 |
| 24 | 5.1/0.65 | 0.124 |
| 48 | 5.7/0.40 | 0.127 |
| 168 | 5.9/0.35 | 0.119 |

TABLE 2

Aluminum Turnings Cutting Oil Reflux Test,
Appearance After 168 Hours Reflux

| Solvent | Amber |
| --- | --- |
| Aluminum Strip | Clean |
| Aluminum Turnings | Clean |
| Mild Steel Strips | Clean |

The stabilized 1,1,1-trichloroethane composition was tested in accordance with the aluminum and aluminum chloride stability test. The solvent appeared cloudy, off-white color with a few dark particles and white flocculent precipitate present. The aluminum turnings appeared clean. Some evolved hydrogen chloride gas was observed at initial boiling, but none was observed after 24 hours reflux.

The stabilized 1,1,1-trichloroethane composition was tested in accordance with the galvanized steel reflux test. The results are shown in Table 3.

TABLE 3

Galvanized Steel Reflux Test

|  | Anhydrous | Hydrous |
| --- | --- | --- |
| Solvent | Colorless | Slightly yellow |
| Strip | Clean | Covered ¾ with brown and white residue |
| pH/Titer | 6.7/0.15 | 6.5/0.60 |
| Water Soluble Chlorides, ppm | <1 | >100 |

EXAMPLE II

The following materials were admixed with industrial grade 1,1,1-trichloroethane to form a stabilized 1,1,1-trichloroethane composition. The concentrations are percentages by weight and are in respect of the final stabilized composition:

| Component | Concentration, percent by weight |
| --- | --- |
| Nitromethane | 0.54 |
| 1,3-dioxolane | 2.6 |
| Secondary Butanol | 1.1 |
| Butylene Oxide (mixed isomers) | 0.30 |
| 1-Nitropropane | 0.55 |
| Acetaldehyde Dimethylhydrazone | 0.001 |

The distillation range of the stabilized 1,1,1-trichloroethane composition was found to be 73.1° C. to 83.1° C. The specific gravity, 25° C./25° C., was 1.311. Initial pH was 6.6. Acid acceptance was 0.168 percent.

pH of the base solvent, i.e., the 1,1,1-trichloroethane without added stabilizers) was 6.7.

A sample of the stabilized composition was evaporated from an inclined plane. No beading or spotting was observed, but there was uneven evaporation.

The stabilized 1,1,1-trichloroethane composition was tested according to the blade aluminum scratch test. The results of three replicates were 1.3, 1.3, 2.

The stabilized 1,1,1-trichloroethane composition was tested according to the aluminum turnings cutting oil reflux test. The results are shown in Tables 4 and 5.

TABLE 4

| Reflux Time, hours | pH | Acid Acceptance, percent |
| --- | --- | --- |
| 0 | 6.9 | 0.191 |
| 24 | 6.7 | 0.178 |
| 48 | 7.0 | 0.188 |
| 168 | 6.3 | 0.157 |

TABLE 2

Aluminum Turnings Cutting Oil Reflux Test,
Appearance After 168 Hours Reflux

| Solvent | Amber |
| --- | --- |
| Aluminum Strip | Clean |
| Aluminum Turnings | Clean |
| Mild Steel Strips | Clean |

The stabilized 1,1,1-trichloroethane composition was tested in accordance with the aluminum and aluminum chloride stability test. The solvent appeared cloudy, off-white color with a few dark particles and white flocculent precipitate present. The aluminum turnings appeared clean. Some evolved hydrogen chloride gas was observed at initial boiling, but none was observed after 24 hours reflux.

The stabilized 1,1,1-trichloroethane composition was tested in accordance with the galvanized steel reflux test. The results are shown in Table 6.

TABLE 6

Galvanized Steel Reflux Test

|  | Anhydrous | Hydrous |
| --- | --- | --- |
| APHA Color of Solvent | 60 | 190 |
| Strip | Clean | Orange corrosion of strip in vapor; strip in solvent was clean |
| pH | 6.6 | 6.5 |
| Water Soluble Chlorides, ppm | 4 | 2 |

The present invention has been described with reference to specific details of certain embodiments thereof, it is not intended that such details should be regarded as limitations upon the scope of the invention except insofar as they are included in the accompanying claims.

We claim:

1. Stabilized 1,1,1-trichloroethane composition which is free of 1,4-dioxane and which consists essentially of (a) 1,1,1-trichloroethane, (b) from about 2 to about 4 percent by weight 1,3-dioxolane, (c) from about 0.25 to about 0.5 percent by weight butylene oxide, (d) from about 0.25 to about 2 percent by weight nitromethane, (e) from about 0.2 to about 0.75 percent by weight 1-nitropropane, (f) from about 0.75 to about 2 percent by weight secondary butanol, and (g) from 0 to about 100 parts per million by weight acetaldehyde dimethylhydrazone.

2. The stabilized 1,1,1-trichloroethane composition of claim 1 wherein the concentration of all stabilizers in said composition is less than of about 7 percent by weight.

3. The stabilized 1,1,1-trichloroethane composition of claim 1 wherein acetaldehyde dimethylhydrazone is present in an amount in the range of from about 5 to about 100 parts per million.

4. The stabilized 1,1,1-trichloroethane composition of claim 1 wherein said composition consists essentially of (a) 1,1,1-trichloroethane, (b) from about 2.5 to about 2.7 percent by weight 1,3-dioxolane, (c) from about 0.3 to about 0.45 percent by weight butylene oxide, (d) from about 0.5 to about 0.7 percent by weight nitromethane, (e) from about 0.35 to about 0.55 percent by weight 1-nitropropane, and (f) from about 1 to about 1.2 percent by weight secondary butanol.

5. The stabilized 1,1,1-trichloroethane composition of claim 1 wherein said composition consists essentially of (a) 1,1,1-trichloroethane, (b) from about 2.5 to about 2.7 percent by weight 1,3-dioxolane, (c) from about 0.3 to about 0.45 percent by weight butylene oxide, (d) from about 0.5 to about 0.7 percent by weight nitromethane, (e) from about 0.35 to about 0.55 percent by weight 1-nitropropane, (f) from about 1 to about 1.2 percent by weight secondary butanol, and about 10 parts per million acetaldehyde dimethylhydrazone.

6. The stabilized 1,1,1-trichloroethane composition of claim 1 wherein 1,1,1-trichloroethane constitutes about 93 percent or more by weight of said stabilized composition.

* * * * *